US00PP17178P2

(12) United States Plant Patent
Howard et al.

(10) Patent No.: US PP17,178 P2
(45) Date of Patent: Oct. 31, 2006

(54) ***EUPHORBIA* PLANT NAMED 'NOTHOWLEE'**

(50) Latin Name: *Euphorbia characias×martinii*
Varietal Denomination: NOTHOWLEE

(76) Inventors: Mark Howard, Notcutts Nurseries, Woodbridge, Suffolk (GB), 1P12 4AF; Simon Leeding, Notcutts Nurseries, Woodbridge, Suffolk (GB), 1P12 4AF ( * ) Notice: Subject to any disclaimer, the term of this patent is extended or adjusted under 35 U.S.C. 154(b) by 0 days.

(21) Appl. No.: 11/225,965

(22) Filed: Sep. 13, 2005

(51) Int. Cl.
*A01H 5/00* (2006.01)

(52) U.S. Cl. ..... Plt./302
(58) Field of Classification Search ..... Plt./302
See application file for complete search history.

(56) References Cited

PUBLICATIONS

Upov–rom GTITM, Plant Variety Database, 2006/01, GTI Jouve Retrieval Software, Citation for *Euphorbia* 'Nothowlee' one page.*

* cited by examiner

*Primary Examiner*—Kent Bell
*Assistant Examiner*—June Hwu

(57) ABSTRACT

A new cultivar of *Euphorbia* named 'NOTHOWLEE' that is distinguished by a compact clumping growth habit, dark purple foliage, and terminal cymes that open into bronze floral heads that completely cover the plant from May through summer. In combination, these characteristics provide a long period of garden interest and set 'NOTHOWLEE' apart from all other existing varieties of *Euphorbia* known to the inventor.

4 Drawing Sheets

Genus: Euphorbia. Species: *characias×martinii*. Denomination: 'NOTHOWLEE'.

BACKGROUND OF THE INVENTION

The present invention relates to a new and distinct cultivar of *Euphorbia*, a hardy perennial that is grown for use as an ornamental landscape plant. The new invention will be referred to hereinafter by the cultivar name 'NOTHOWLEE'.

'NOTHOWLEE' was discovered by the inventors in April 2002 in Woodbridge, Suffolk, England. The inventors first observed 'NOTHOWLEE' as a naturally occurring single whole plant which was found by the inventors to be growing within a commercial crop of the variety of *Euphorbia* named 'Charam' U.S. Plant patent application Pending, Ser. No. 09/944,932, filed Aug. 31, 2001). The inventors observed that the foliage of 'NOTHOWLEE' was strikingly different from the foliage of the surrounding plants of 'Charam'. The foliage of 'NOTHOWLEE' is predominantly dark purple in coloration whereas the foliage of 'Charam' is the typical mid green for the species and hybrids of *Euphorbia martinii* and *Euphorbia characias*.

The inventors removed 'NOTHOWLEE' from the crop of 'Charam' and continued to observe 'NOTHOWLEE' as it came into flower. The flowers which take the form of terminal cymes appear first as a bronze canopy which complements the dark purple foliage.

The closest comparison plant to 'NOTHOWLEE' known to the inventors is the parent variety, 'Charam'. Whereas 'NOTHOWLEE' has similar growth habit to 'Charam', the colors of the foliage of 'NOTHOWLEE' and 'Charam' are dark purple and mid green respectively; and the colors of the inflorescence of 'NOTHOWLEE' and 'Charam' are bronze and yellow respectively.

The first asexual reproduction of 'NOTHOWLEE' was accomplished by the inventors using the method of tip cuttings and was carried out in June 2002 in Woodbridge, Suffolk England. The inventors determined that the plants that grew from this first asexual reproduction appeared to be identical to the original single plant of 'NOTHOWLEE'. Subsequent generations which have been propagated similarly have confirmed to the inventors that 'NOTHOWLEE' is a stable variety which reproduces true to type.

The inventors have filed an application for a grant of European Community Plant Breeders Rights, serial number 2004/0626, filed Mar. 30, 2004.

The first public sale or distribution of plants of 'NOTHOWLEE' took place on Apr. 6, 2005 in Woodbridge, Suffolk, England.

SUMMARY OF THE INVENTION

The following traits have been repeatedly observed and represent the distinguishing characteristics of 'NOTHOWLEE'. These traits in combination distinguish 'NOTHOWLEE' from all other existing varieties of *Euphorbia*. 'NOTHOWLEE' has not been tested under all possible conditions and phenotypic differences may be observed with variations in environmental, climatic, and cultural conditions, however, without any variance in genotype.

1. *Euphorbia* 'NOTHOWLEE' exhibits a compact clumping growth habit.
2. *Euphorbia* 'NOTHOWLEE' exhibits terminal cymes which open bronze in March and develop a complete canopy by April remains through to July.
3. *Euphorbia* 'NOTHOWLEE' is evergreen in USDA zones 7 and higher and offers a long period of garden interest.

4. *Euphorbia* 'NOTHOWLEE' is a complete 'hummock' of flower color when in full bloom.
5. *Euphorbia* 'NOTHOWLEE' is hardy to minus 12° Centigrade.
6. *Euphorbia* 'NOTHOWLEE' is 70 cm. in height and 70 cm. in width at maturity.

BRIEF DESCRIPTION OF THE DRAWINGS

The accompanying drawings illustrate the distinguishing traits of the new cultivar 'NOTHOWLEE'. The drawings have been made from photographs which were taken in spring and summer using plants that were 12–15 months old from a cutting.

The drawing labeled as FIG. 1 depicts a single whole plant of 'NOTHOWLEE' which has been planted outside in Woodbridge, Suffolk, England. The illustrated plant is approximately 14 months old and is in its early flowering stage. This drawing depicts the compact mounding habit of 'NOTHOWLEE' and its dark purple foliage and bronze colored inflorescence.

Figure 1:
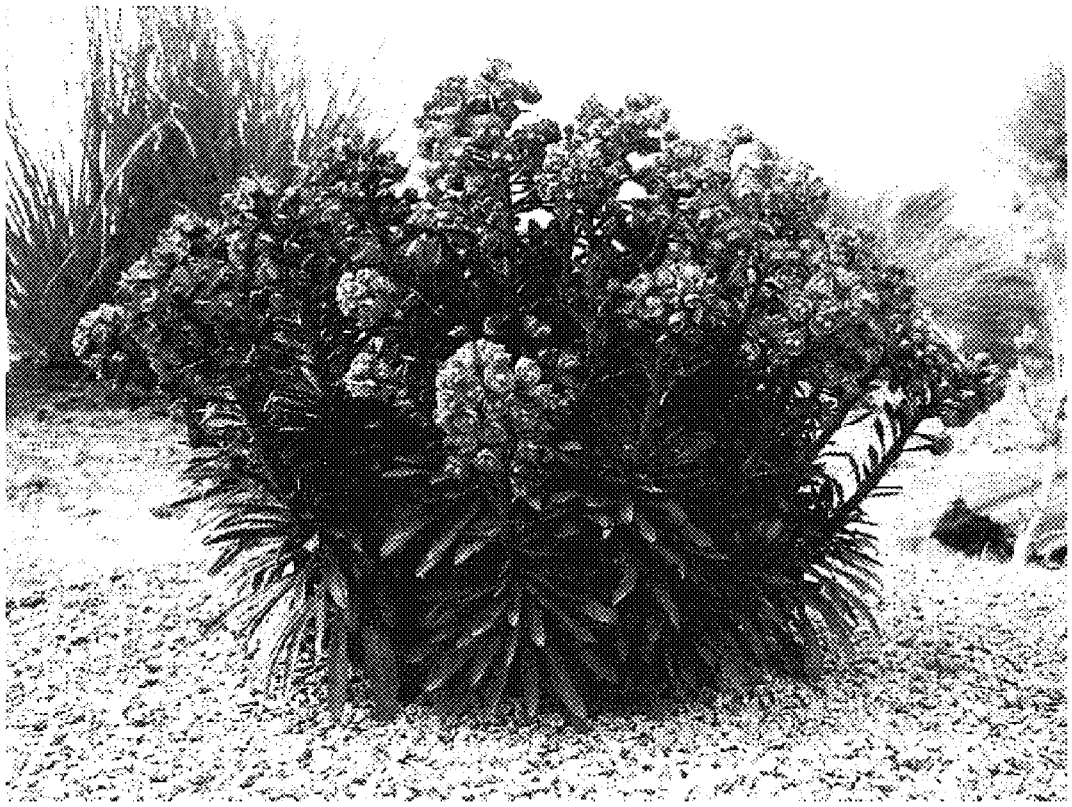
Figure 2:
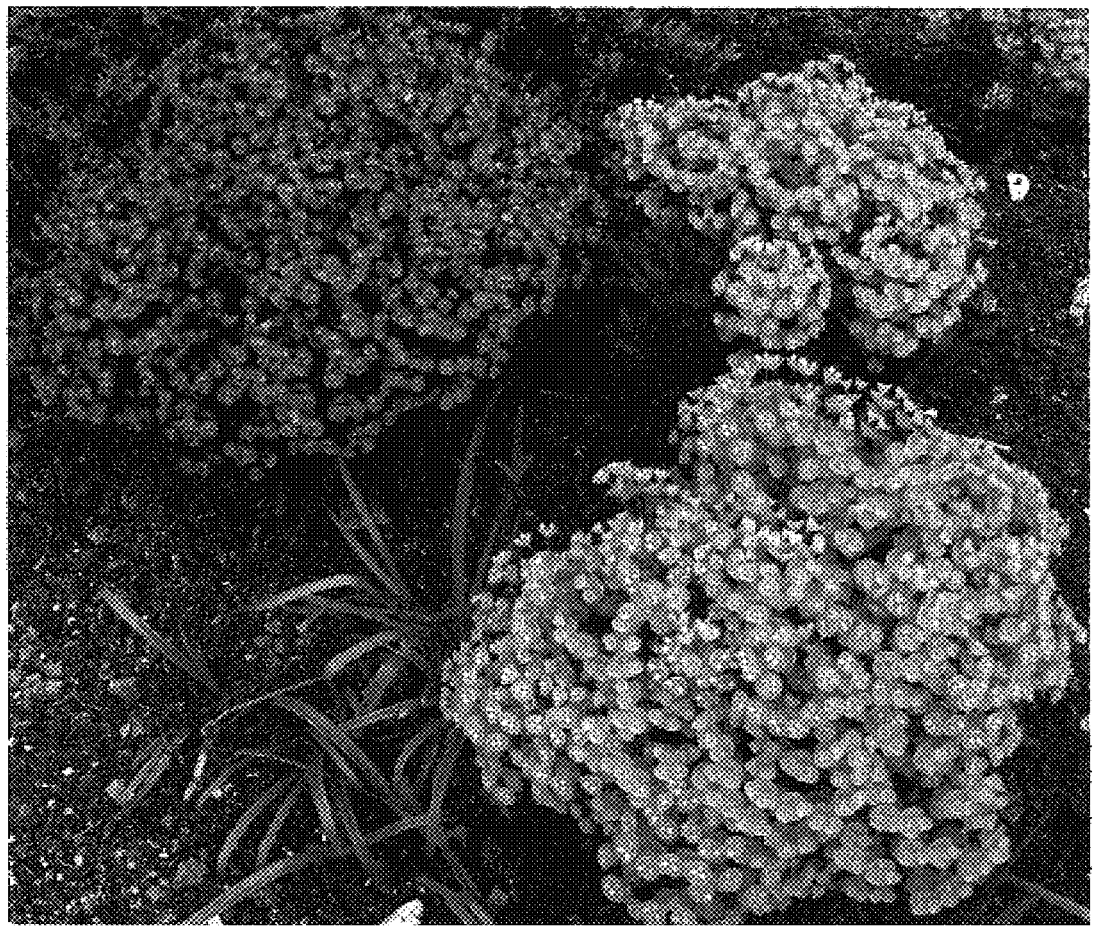

The drawing labeled as FIG. 2 illustrates both 'NOTHOWLEE' and its parent 'Charam' as one year old plants in the open ground. 'NOTHOWLEE' appears as a single plant in the upper left of the drawing. 'Charam' appears as two plants, one in the foreground and one in the upper right of the drawing. Both varieties are shown with their characteristic canopy of flower by mid summer. The drawing illustrates the comparative colorations of the inflorescence, that of 'NOTHOWLEE' being bronze; that of 'Charam' being yellow-green.

Figure 3:
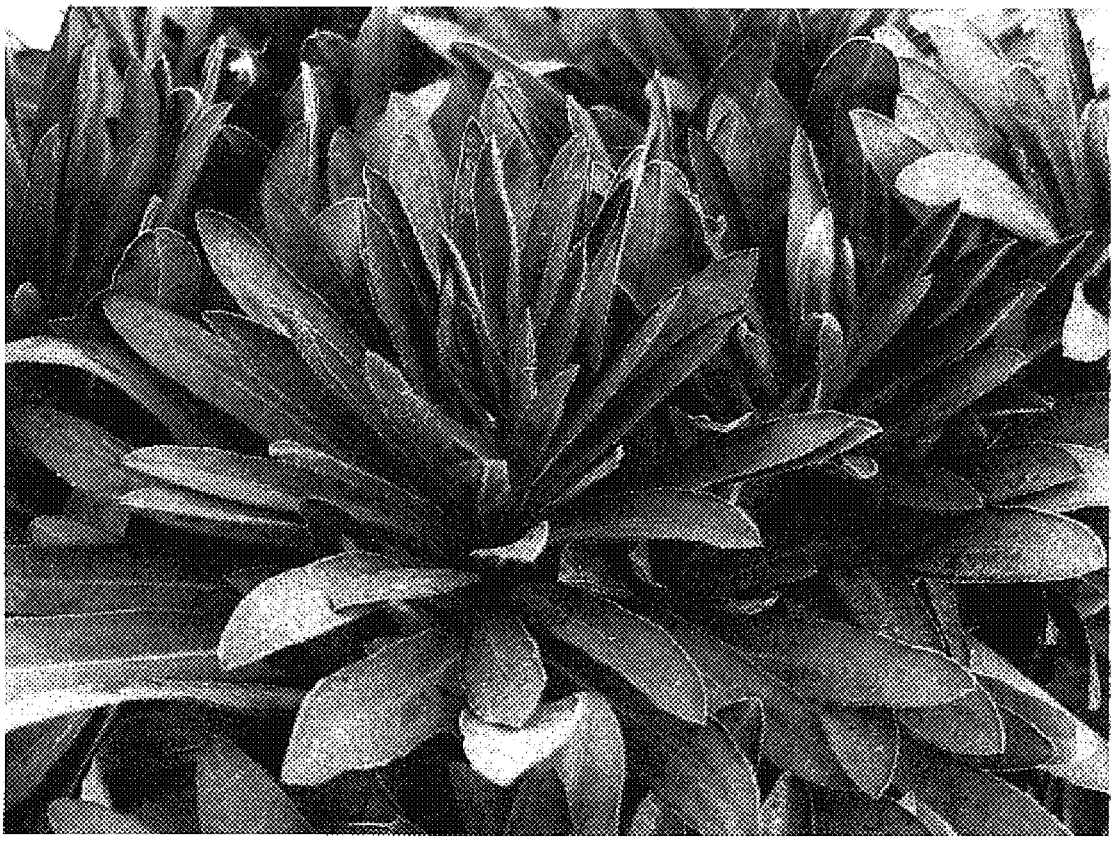

The drawing labeled as FIG. 3 presents a close-up view of the new spring foliage growth of 'NOTHOWLEE', at approximately 12 months from the initial cutting and before the initiation of any flower.

Figure 4:
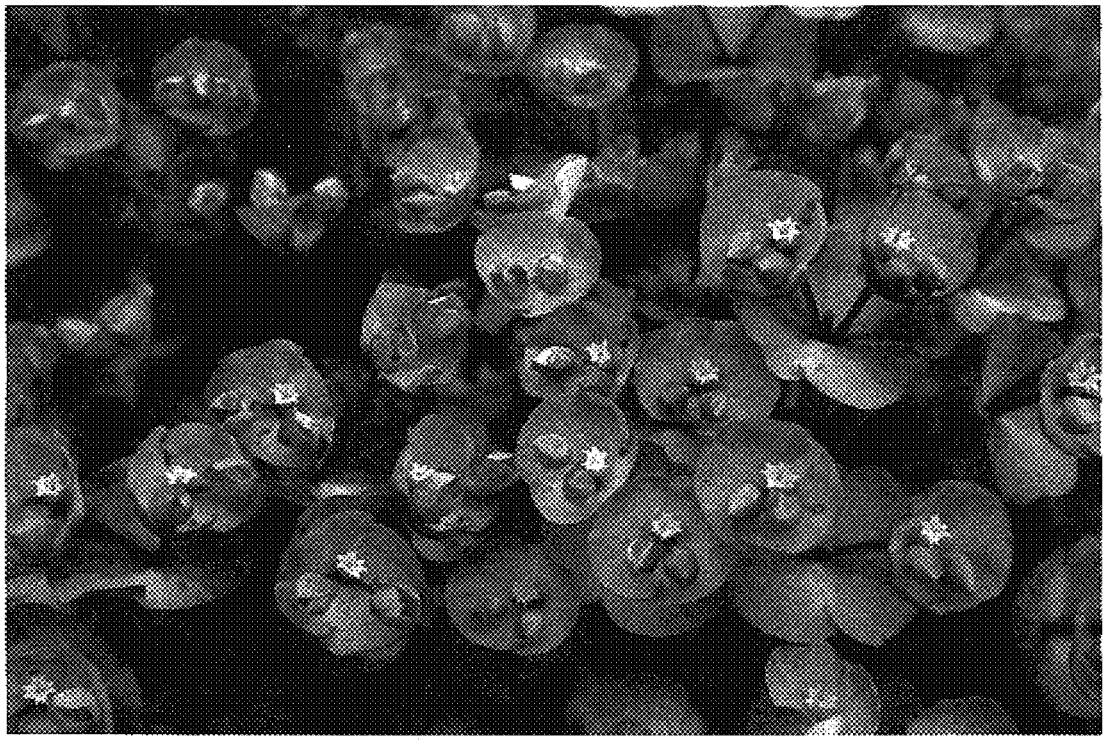

The drawing labeled as FIG. 4 presents a close-up view of the inflorescence of 'NOTHOWLEE' as it appears in mid summer when the inflorescence canopy is fully developed.

The drawings have been made from photographs taken by conventional photographic techniques and although flower and foliage colors in the photographs may appear different from actual colors due to light reflectance, they are as accurate as possible by conventional photography.

BOTANICAL DESCRIPTION OF THE PLANT

The following is a detailed botanical description of the new *Euphorbia* cultivar 'NOTHOWLEE'. Observations, measurements, values and comparisons have been collected in spring in Woodbridge, Suffolk, England from plants that were three years old and grown out of doors in garden soil. Color determinations are made in accordance with the 2001 edition of The Royal Horticultural Society's Colour Chart, except where general color terms of ordinary dictionary significance are used. The growing requirements of the new variety are similar to the species and there are no known growing problems, diseases or pests.

Botanical classification: *Euphorbia* 'NOTHOWLEE'.
Common name: Spurge.
Parentage: *Euphorbia* 'NOTHOWLEE' is a naturally occurring whole plant mutation of Euphorbia 'Charam'. 'Charam' arose as a seedling that resulted from the spontaneous hybridization of the following parents:
- *Female parent of 'Charam'.*—*Euphorbia characias* sub sp.*wulfenii* 'Purple and Gold'.
- *Male parent of 'Charam'.*—*Euphorbia martinii.*

Propagation method: Terminal stem cuttings.
Rooting habit: Fibrous rooting habit.
Time to develop roots: Approximately 2–3 weeks are required for roots to develop on an initial cutting, and a further 2–3 months for that cutting to produce a plug or liner suitable for potting into finished containers.
Crop time: Approximately 6–8 months are required to develop a finished one liter container from a rooted plug or liner.
Growth habit: Upright, compact and clumping growth habit.
Use: Ornamental landscape plant.
Type: Perennial herb.
Vigor: Vigorous.
Height of plant: 50–70 cm. in height.
Width of plant: 50–70 cm. in width.
Sexuality: 'NOTHOWLEE' is assumed to be monoecious with rudimentary stamens that mature after the female parts.
Cultural requirements: Plant in full sun and well-drained soil.
Hardiness: Hardy to minus 12° Centigrade.
Stem:
- *Branching habit.*—Upright.
- *Trunk dimensions.*—2 cm. in diameter and 3 cm. from soil level to first branching.
- *Stem color.*—Mostly 59A with streaks of 144A.
- *Stem shape.*—Cylindrical to columnar.
- *Stem width.*—0.75 cm. in diameter.
- *Stem length.*—30 cm. in length.
- *Internode length.*—0.50 cm. between nodes.
- *Stem surface.*—Mostly smooth with some pubescence. Basal surface to mid-stem is heavily covered with bundle scars. Some terminal stem surfaces are rugose.
- *Bundle scars.*—Present on stem surface.
- *Shape of bundle scars.*—Linear shaped.
- *Dimensions of bundle scars.*—3 mm. in length and 1 mm. in width.
- *Color of bundle scars.*—199D.
- *Quantity of bundle scars.*—Numerous amounting to approximately 42 on a 20 cm. long stem.
- *Stem texture.*—Fleshy and flexible.
- *Color of pubescence.*—198D.
- *Other.*—Plant parts exude a white milky sap that can be toxic and can elicit dermal irritation.

Foliage:
- *Type.*—Evergreen.
- *Leaf arrangement.*—Whorled.
- *Leaf division.*—Simple.
- *Leaf shape.*—Oblanceolate to spatulate.
- *Mature leaf length.*—9 cm. in length.
- *Mature leaf width.*—1 cm. in width.
- *Young leaf length.*—2.5 cm. in length.
- *Young leaf width.*—0.75 cm. in width.
- *Internode length.*—1 cm. between nodes.
- *Leaf apex.*—Acuminate.
- *Leaf base.*—Truncate.
- *Quantity of leaves.*—Numerous amounting to approximately 25 leaves on a 7 cm. long stem.
- *Leaf venation pattern.*—Pinnate pattern with a barely visible mid-vein on the adaxial surface and a prominent protruding mid-vein on the abaxial surface.
- *Vein color* (*adaxial surface*).—137B.
- *Vein color* (*abaxial surface*).—138B.
- *Margin.*—Entire.
- *Leaf surface* (*abaxial surface*).—Pubescent.

*Leaf surface* (*adaxial surface*).—Sparsely puberulent.
*Color of pubescence.*—198D.
*Leaf attachment.*—Sessile.
*Mature leaf color* (*adaxial surface*).—136B tinged with N79A.
*Mature leaf color* (*abaxial surface*).—138B tinged with N79A.
*Young leaf color* (*adaxial surface*).—Mostly N79B tinged with 137B.
*Young leaf color* (*abaxial surface*).—Mostly N79B with streaks of 137C.

Flower:
*Inflorescence.*—Terminal cyme.
*Dimensions of inflorescence.*—7 cm. in length and 4 cm. in width.
*Flowering season.*—Late winter until late spring.
*Peduncle dimensions.*—15 cm in length and 2 mm. in width.
*Peduncle color.*—144A with tinge of 79A.
*Peduncle surface.*—Sparsely puberulent.
*Pedicels lengths.*—Approximately 5 mm for the shorter pedicels and approximately 5 cm for the longer pedicels.
*Color of pubescence.*—198D.
*Petals.*—Apetalous.
*Sepals.*—Asepalous.
*Floral leaf attachment.*—Connate perfoliate.
*Dimensions of floral leaves.*—12 mm. in length and 2 cm. in width.
*Shape of floral leaf.—Closest to reniform.*
*Color of floral leaf.*—143B with streaks of 59C.
*Number of floral leaves.*—Two in number.
*Fused or unfused.*—Basally fused.
*Internode length.*—5–6 cm. between nodes.
*Number of cyathium.*—Two cupped within the center of two basally fused floral leaves.
*Shape of cyathium.*—Cupulate.
*Number of floral leaves on each cyathium.*—Two.
*Fused or unfused.*—Basally fused.
*Shape of floral leaves on cyathia.*—Closest to reniform.
*Color of cyathium.*—144C with streaks of 59C.
*Dimensions of cyathium.*—5 mm. in length and 6 mm. in width.
*Nectary.*—Four flattened glands on four fused bracts.
*Shape of nectary.*—Flattened crescent shaped glands with two horns.
*Dimensions of nectary.*—6 mm in height and 6 mm. in diameter.
*Color of mature nectary.*—161B.
*Color of young nectary.*—154C.
*Position of nectaries.*—One green nectary in the center of each cyathium and one yellow nectary axillary to the floral leaf and basal to each pair of cyathia.
*Lastingness of the inflorescence.*—10–15 days on the plant.

Reproductive organs:
*Stamens.*—Six rudimentary stamens that are visible with a lens after the female parts have matured.
*Stamen color.*—200A.
*Stamen dimensions.*—Less than 0.25 mm. in length and less than 0.25 mm. in diameter.
*Anther shape.*—Oval to round.
*Anther color.*—200A.
*Ovary dimensions.*—1.5 mm. in width and 1.5 mm. in length.
*Shape of ovary.*—Globose.
*Position of ovary.*—Superior.
*Color of ovary.*—143A.
*Pollen.*—Absent.
*Pistil.*—One in number.
*Color of pistil.*—143A.
*Dimensions of pistil.*—7 mm. length and less than 1 mm. in width.
*Style.*—Three in number.
*Style shape.*—Bifid.
*Style color.*—143A.
*Style dimensions.*—Less than 1 mm. in width and 1 mm. in height.
*Stigma.*—Six in number.
*Stigma color.*—59A.
*Dimensions of stigma.*—Less than 0.75 mm. in width and less than 0.75 mm. in height.

Seed: Seed has not been observed.

It is claimed:

1. A new and distinct cultivar of *Euphorbia* plant named 'NOTHOWLEE' as described and illustrated.

* * * * *